United States Patent [19]

Anderson et al.

[11] Patent Number: 4,485,813
[45] Date of Patent: Dec. 4, 1984

[54] IMPLANTABLE DYNAMIC PRESSURE TRANSDUCER SYSTEM

[75] Inventors: Kenneth M. Anderson, Bloomington; Dennis A. Brumwell, New Brighton, both of Minn.

[73] Assignee: Medtronic, Inc., Minneapolis, Minn.

[21] Appl. No.: 322,814

[22] Filed: Nov. 19, 1981

[51] Int. Cl.³ ............................................. A61B 5/02
[52] U.S. Cl. ................................... 128/675; 128/419 P
[58] Field of Search ................ 128/631, 642, 670–675, 128/700, 748, 419 P, 419 D, 419 PG, 903

[56] References Cited

U.S. PATENT DOCUMENTS

| Re. 30,372 | 8/1980 | Mirowski et al. | 128/419 D |
| 3,294,988 | 12/1966 | Packard | 128/675 X |
| 3,545,275 | 12/1970 | Harrison et al. | 128/675 X |
| 3,659,615 | 5/1972 | Enger | 128/419 P |
| 3,942,536 | 3/1976 | Mirowski et al. | 128/419 D |

OTHER PUBLICATIONS

Augelakos, E. T., "Semiconductor Pressure Microtransducers for Measuring Velocity & Acceleration of Intraventricular Pressures", American Journal of Medical Electronics, Oct.-Dec., 1964, pp. 266–270.

Primary Examiner—Kyle L. Howell
Assistant Examiner—Francis J. Jaworski
Attorney, Agent, or Firm—Robert C. Beck; John L. Rooney; Joseph F. Breimayer

[57] ABSTRACT

Pressure and motion transducer, and cooperating circuitry for an implantable medical device is disclosed. The system includes a clock for the pulse excitation of a dynamic motion transducer and further includes circuitry for recovering the modulated signal from the transducer.

10 Claims, 7 Drawing Figures

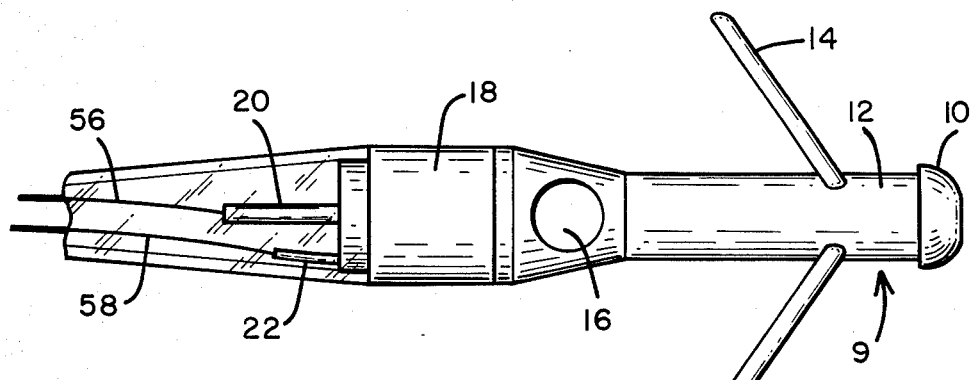
Fig. 1
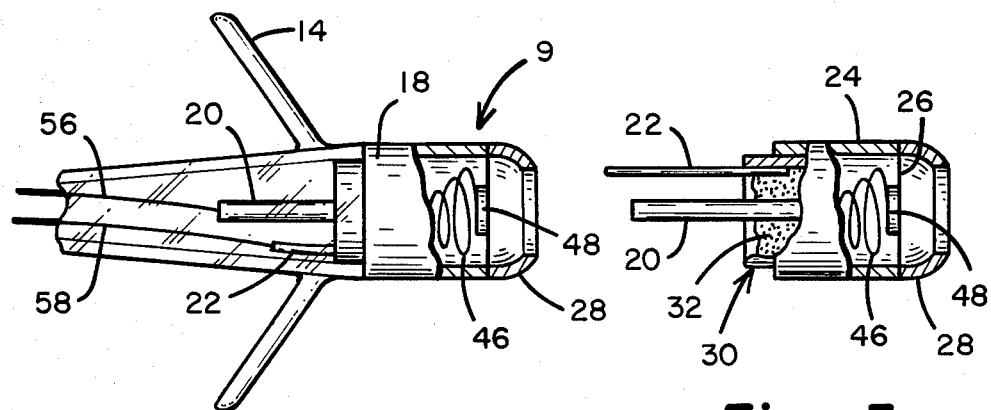
Fig. 2
Fig. 3
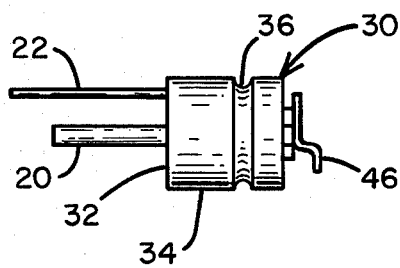
Fig. 4
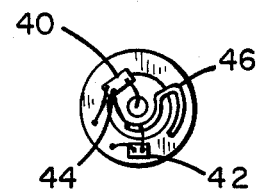
Fig. 5

IMPLANTABLE DYNAMIC PRESSURE TRANSDUCER SYSTEM

BACKGROUND OF THE INVENTION

1. Field of the Invention

This invention relates to implantable medical devices and, more particularly, to a dynamic motion transducer system for use in a chronically implanted medical device. More specifically, the invention discloses a transducer and circuitry suitable for dectecting pressure and other force parameters for use with a pacemaker or other implanted cardiac monitoring and/or treatment device.

2. Description of the Prior Art

Pressure transducers for measuring fluid pressure within the human body are well known in the art from U.S. Pat. No. 4,023,526 to Hynecek, et al. Devices such as that disclosed by Hynecek are typically used in an invasive fashion for temporary diagnostic purposes. Such devices are typically interfaced to signal processing circuitry located in diagnostic equipment located outside of the patient's body.

Recent increases in the complexity of pacemakers and other implantable medical devices have increased efforts at producing sensors and transducers to monitor a variety of physiologic functions. These transducers will allow the exploitation of the additional capability of such medical devices.

A successful sensor or transducer system must have a life expectancy as long as the implanted device which may be as long as ten years in the case of a lithium battery powered pacemaker. Such sensors must be hermetically sealed and must operate at very low current. Additionally, these features must be attained in a device small enough to be passed down a human vein or artery. For these reasons, the aforementioned prior art transducers are not suited for chronic implant applications.

SUMMARY OF THE INVENTION

By way of contrast, the implantable dynamic pressure transducer system of the present invention is suitable for use in a chronically implanted medical device. The system includes a simple piezoelectric crystal which converts a physiologic force signal into a voltage. Buffering circuitry hermetically sealed with the crystal lowers the impedance of the pressure signal and transmits it through a lead system to the implanted medical device. Within the device the signal is recovered and used by the medical device.

BRIEF DESCRIPTION OF THE DRAWINGS

FIG. 1 is a partial phantom view of a first embodiment of the transducer and circuitry of the present invention incorporated in a cardiac pacing lead, FIG. 2 is a partial phantom view of a second embodiment of the transducer and circuitry of the present invention incorporated in a pacing lead, FIG. 3 is a side elevation view of the pressure monitoring capsule incorporated into the leads of FIGS. 1 and 2, FIG. 4 is a side elevation showing the detail of the mechanical construction of the pressure capsule of FIG. 3, FIG. 5 is an end view of the pressure capsule of FIG. 3 or 4 showing the location of the circuitry upon the electrical substrate of the pressure capsule.

DESCRIPTION OF THE PREFERRED EMBODIMENT

Figure 6:
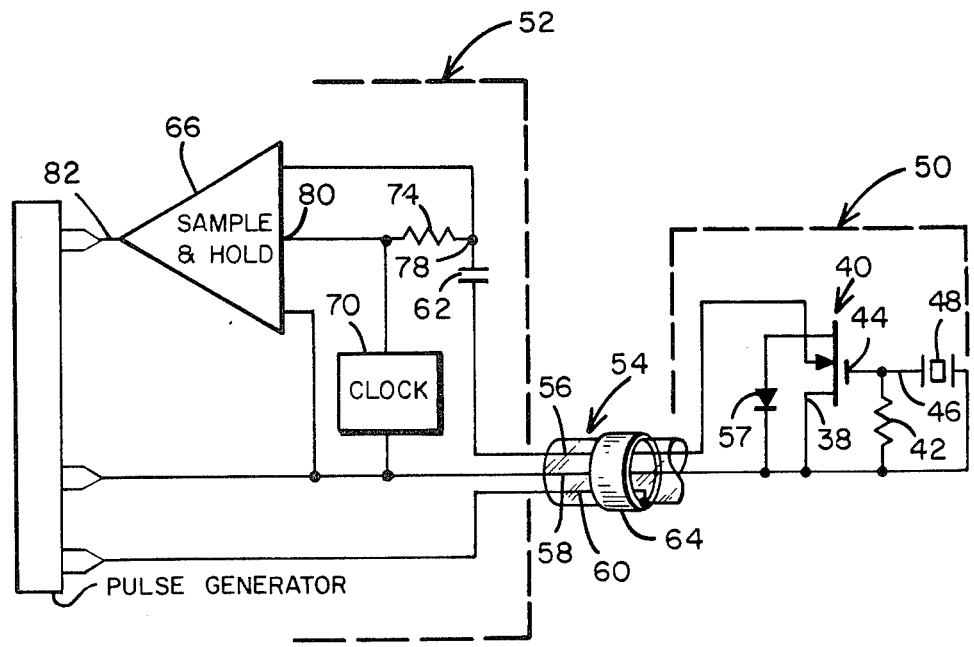
FIG. 6 is a schematic diagram illustrating a method of interfacing the invention within the context of a cardiac pacer and, FIG. 7 is a waveform diagram showing the relationship between various signals in the pressure transducer system.

Turning to FIG. 1, there is shown a body implantable lead 9. The lead incorporates a pacing electrode 10 located at the proximal end of the lead body 12. Flexible tines 14 are located on this body to fix the lead in cardiac tissue in the manner taught by U.S. Pat. No. 3,902,501 to Citron et al, which is incorporated by reference herein. A port 16 provides fluid communication to pressure and motion sensing capsule 18 located in a spaced relation from the pacing electrode 10. Electrical connections 20, and 22 are provided to the electronic components within capsule 18. The configuration of FIG. 1 has been shown to be effective when intracardiac pressure information is sought. The section of the lead body between the tip 10 and the port 16 may be made from relatively rigid material or it may incorporate a flexible coil to provide a flexible lead body.

The configuration of FIG. 2 locates the sensing capsule 18 at the proximal end of the lead. Fixation elements such as flexible tines 14 are located proximate to the capsule to engage the sensing capsule in cardiac tissue. This configuration is effective when corruption of the pressure signal by noise due to cardiac muscle activity can be tolerated, or when ventricular motion is of primary interest.

The lead configuration of FIG. 1 is preferred in applications where pure pressure information is the principle signal of interest. Such applications include the detection of the patients respiration rate which may be recovered from the intracardiac pressure signal.

The lead configuration of FIG. 2 is preferred when the motion of ventricular tissue is the principle signal is of interest. Applications for this configuration include the detection of ventricular fibrillation by a direct measure of muscle motion.

The pressure and motion sensing capsule is shown in isolation in FIG. 3. The capsule is formed from a cylindrical member 24 which is manufactured from a body inert material such as titanium. A thin metallic membrane 26 is positioned across the cylinder 24 to form a sensing diaphragm. This diaphragm may also be manufactured from titanium. An annular nose piece 28 is located adjacent to the diaphragm 26 to protect it. These elements, including the cylinder 24, diaphragm 26 and nose piece 28 may be welded together to produce a unitary structure providing a hermetic seal between the diaphragm and the cylinder.

The rear portion of the cylinder 24 is plugged with a feedthru assembly 30, as shown in FIG. 4, which retains conductors 20 and 22 and which forms a hybrid substrate for various electronic elements, to be described in connection with FIGS. 5 and 6.

It is preferred to form the insulative section 32 of the feedthru from epoxy or a ceramic material.

This insulative section is encased in a cylindrical metallic collar 34 which contains an annular recess 36 to facilitate hermetic assembly.

The positioning of the sensors electronic components is shown in FIG. 5. A field effect transistor 40 (FET) die is located on the epoxy 32. The source pad 38 of the FET is wire bonded to the collar 34. A chip resistor 42 is bonded to the collar 34 and a wire bond connection 37 is made to the collar 34. The drain pad of FET 39 is wire bonded to the pin forming electrical connection 20. The gate 44 pad is bonded to a wire 46 which is electrically connected to one side of crystal 48. The crystal itself is rigidly attached to diaphragm 26 so that movement of the diaphragm causes the crystal to flex. The crystal is made from a piezoelectric material such as barium titinate which acts as a high impedance voltage source in response to diaphragm deflections.

The schematic diagram of FIG. 6 shows the electrical connections previously described. The sensor capsule electronics are shown generally as 50 while the interfacing, signal recovery, and sensor excitation electronics are shown generally as 52. As previously described, the sensor electronics are located in the lead and the excitation electronics are contained within the implanted medical electronic device. The lead system 54 connects the two electronic systems. In practice, the lead system will include a plurality of flexible conductors 56, 58, 60, which are embedded in a flexible lead body 12. Typically, the lead body will be manufactured from medical grade silicone rubber or urethane and will have a length of several centimeters. The electrical configuration of the sensor permits one of the two conductors associated with the sensor electronics to be shared with the pacing function. The conductors 58, 56 and 60 may be formed from multiple filaments spiral wound conductors. To provide the additional required electrode for bipolar pacing stimulation, a ring electrode 64 may be provided on the lead body as shown in FIG. 6. For the unipolar pacing configuration, the external can of the pacemaker device becomes the indifferent electrode, and ring electrode 64 and its associated conductor 60 need not be provided.

The crystal 48 is a two-terminal piezoelectric device producing a voltage on wire 46 proportional to the rate of mechanical deflection applied to the membrane 26 by the physiologic force. The crystal 48 is loaded by a 20 gigaohm load resistor 42 which forms a high pass filter network with the associated capacitance of the pressure transducer 48. This modified signal is applied to the gate 44 of the enhancement mode FET. The FET circuitry is configured as a source-following voltage buffer and produces a drain to source voltage proportional to the voltage applied to gate 44.

In operation, a potential is provided between the source 38 and drain connections 44 of FET by clock 70. Periodic clock pulses are coupled through coupling capacitor 62 to the lead system producing a periodic excitation of the sensor circuitry. This excitation is shown by waveform B in FIG. 7 which is a representation of the output of clock 70 as applied to the sensing resistor 74. Waveform C of FIG. 3 is the recovered signal from the pressure transducer circuitry located in the hermetic can as measured at node 78. The difference in amplitude between successive pulses of waveform C is due to the variation in source and drain resistance produced by the application of a voltage signal to the gate of the FET.

Figure 7:
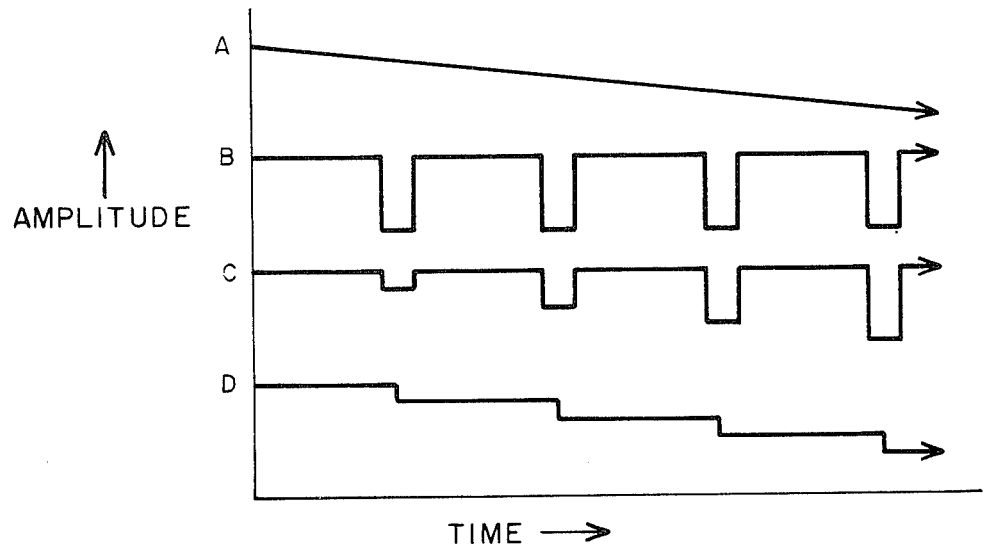

The waveform recovered from the pressure transducer shown in FIG. 7 as waveform C is translated into waveform D by the sample and hold circuit 66. This sample and hold circuitry samples the recovered signal at node 78 at time intervals determined by clock 70. The inputs to the sample and hold circuitry 66 include the voltage at node 78, and clock input 70. The output of the sample and hold circuit available at terminal 82 is shown as waveform D of FIG. 3 which corresponds to the mechanically applied physiological signal shown as waveform A.

Additionally, it is important to note that the pressure signal applied to the transducer, shown as waveform A is the full band width signal applied to the pressure transducer. However, by changing the load resistance 42, one may produce a time derivative of the applied pressure signal which may be of more significance or usefulness for monitoring physiological activity within the heart itself. Another detail of circuit operation indicated in FIG. 6 is the existence of the substrate diode 57 between the source and ground reference connections of the FET transistor. This substrate diode is formed during the manufacturing of the FET and is used to protect the device during handling. The substrate diode, however, does have an effective circuit function within the present invention since it effectively clamps the maximum excursion of the source voltage and, therefore, permits the transducer to be operated through a capacitor such as 62, eliminating the possibility of accidental DC excitation of the heart and allowing the circuit to be operated at voltages outside the normal positive and negative battery potentials of the medical device 52.

What is claimed is:

1. An implantable dynamic pressure and motion transducer system for use in an implantable medical device comprising:
    a force responsive transducer for converting a physiological signal into a corresponding electrical signal;
    buffer amplifier means, receiving said transducer electrical signal, and producing an amplified output signal;
    clock means for generating energizing pulses coupled to said buffer amplifier and said transducer for periodically activating said buffer amplifier and transducer; and
    signal recovery means responsive to said output signal for recovering a signal corresponding to said physiological signal.

2. The implantable dynamic pressure and motion transducer system of claim 1 further including:
    a hermetic sensor capsule for containing said force transducer and said buffer amplifier;
    a hermetic device can for containing said signal recovery means and additional signal utilization circuitry; and
    a lead system for interconnecting said sensor capsule and said device can.

3. The implantable dynamic pressure and motion transducer of claim 1 or 2 wherein:
    said buffer amplifier comprises a metal oxide field effect transistor (FET) operated in voltage-follower configuration with said transducer signal applied to the gate of said FET.

4. The implantable dynamic pressure and motion transducer of claim 3:
    wherein the drain connection of said FET is in common with one pacing terminal; and
    a pacing pulse generator for providing a stimulus to at least one pacing terminal for delivering stimulating energy to said organ.

5. An implantable dynamic pressure and motion transducer for use with an implantable pacer system of the type having a pulse generator for generating an electric stimulus pulse on a pacing electrode comprising:

a force responsive transducer for converting a physiological force signal into a corresponding electrical signal;

said transducer being incorporated in a transducer capsule incorporated in turn in a lead body for placement in cardiac tissue;

buffer amplifier means adapted to receive said electrical signal, and producing an amplified output signal;

said buffer amplifier means being incorporated in said transducer capsule;

clock means for generating energizing pulses coupled to said buffer amplifier and said transducer for periodically activating said buffer amplifier and said transducer;

signal recovery means responsive to said output signal for recovering a signal corresponding to said physiological signal.

6. The device of claim 5 wherein said lead body includes:

multiple conductors embedded in a flexible body inert material; and said conductors being electrically connected to said transducer capsule to couple said implantable pacer.

7. The device of claim 6 including tines on said lead body positioning said transducer capsule in cardiac tissue to monitor the motion of the cardiac tissue.

8. The device of claim 6 including tines on said lead body for positioning said transducer capsule remote from cardiac tissue to monitor intracardiac pressure variations.

9. The device of claim 8 wherein said buffer amplifier is configured to provide full bandwidth pressure information to said signal recovery means.

10. The device of claim 8 wherein said buffer amplifier is configured to provide the time derivative of said physiological force signal to said signal recovery means for detecting cardiac pumping.

* * * * *